United States Patent [19]

Welply et al.

[11] Patent Number: 5,151,445
[45] Date of Patent: Sep. 29, 1992

[54] METHOD OF INHIBITING PARASITIC ACTIVITY

[75] Inventors: Joseph K. Welply, St. Peters; Steven P. Adams, St. Charles; Jeffrey I. Gordon, Olivette, all of Mo.

[73] Assignee: Washington University, St. Louis, Mo.

[21] Appl. No.: 638,709

[22] Filed: Jan. 8, 1991

Related U.S. Application Data

[63] Continuation-in-part of Ser. No. 208,192, Jun. 16, 1988, abandoned, which is a continuation-in-part of Ser. No. 151,774, Feb. 3, 1988, abandoned.

[51] Int. Cl.$^5$ .............................................. A61K 31/19
[52] U.S. Cl. ................................ 514/557; 514/558; 514/560
[58] Field of Search ........................ 514/557, 558, 560

[56] References Cited

U.S. PATENT DOCUMENTS

| | | | |
|---|---|---|---|
| 2,154,850 | 4/1939 | Kaufmann | 167/43 |
| 2,467,884 | 4/1949 | Elias | 167/58 |
| 4,406,884 | 9/1983 | Fawzi et al. | 424/81 |

FOREIGN PATENT DOCUMENTS

| | | |
|---|---|---|
| 327523 | 8/1989 | European Pat. Off. . |
| 2035751 | 12/1970 | France . |
| 5094317 | 1/1979 | Japan . |

OTHER PUBLICATIONS

Bryant et al CA112:48304k 1989.
Low, Biochem. J. 244, 1–13 (1987).
Ferguson, Science 239, 753–759 (1988).
Ferguson & Cross, J. Biol. Chem. 259, 3011–3015 (1984).
Ferguson et al., Ibid. 260, 4963–4968 (1985).
Heuckeroth et al., J. Biol. Chem. 263, 2127–2133 (1988).
Heuckeroth et al., Proc. Natl. Acad. Sci. USA 85, 8795–8799 (1988).
Heuckeroth et al., Proc. Natl. Acad. Sci. USA 86, 5262–5266 (1989).
Bryant et al, Proc. Natl. Acad. Sci. USA 86, 8655–8659 (1989).

Primary Examiner—Frederick E. Waddell
Assistant Examiner—Russell Travers
Attorney, Agent, or Firm—Scott J. Meyer

[57] ABSTRACT

A method of inhibiting parasitic activity is disclosed in which the biosynthesis of the glycosyl phosphatidylinositol (GPI) anchor of said parasite is inhibited by incorporating into said GPI anchor an oxy-substituted fatty acid analog in place of myristate. The inhibitory compounds ar $C_{13}$ and $C_{14}$ fatty acids or alkyl esters thereof in which a methylene group normally in carbon position 4 to 13 of said fatty acid is replaced with oxygen.

6 Claims, 4 Drawing Sheets

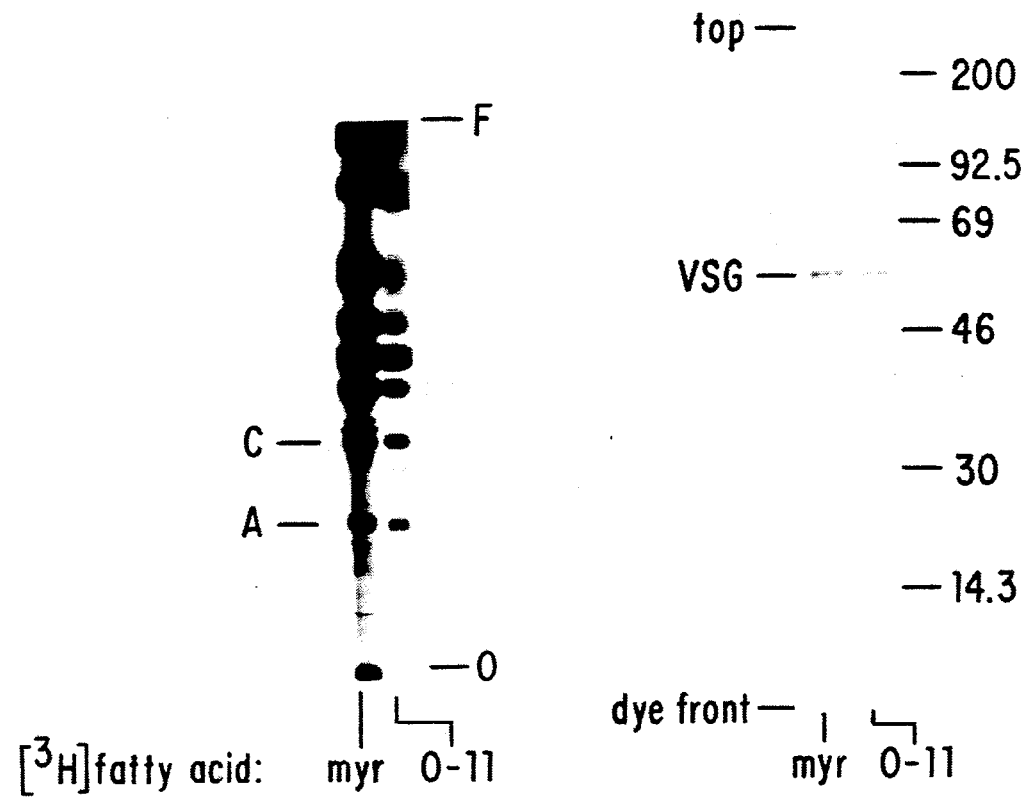
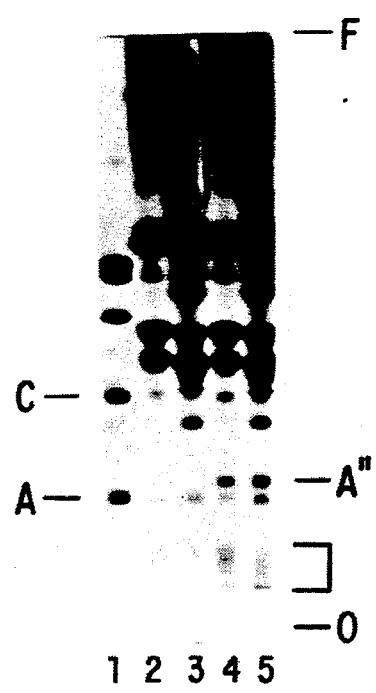
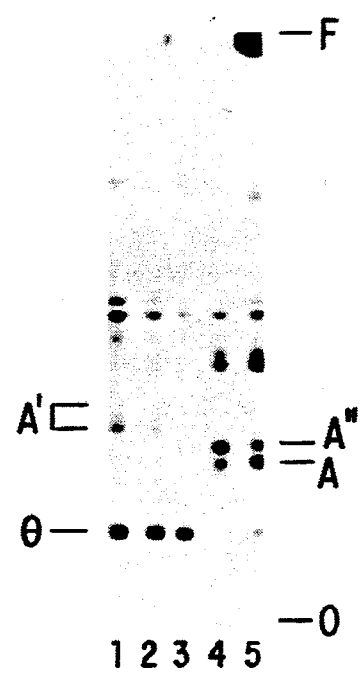
FIG. 1A  FIG. 1B
FIG. 2A  FIG. 2B

METHOD OF INHIBITING PARASITIC ACTIVITY

CROSS-REFERENCE TO RELATED APPLICATION

This is a continuation-in-part of copending application Ser. No. 07/208,192, filed June 16, 1988, now abandoned, which is a continuation-in-part of application Ser. No. 151,774, filed February 3, 1988, now abandoned.

BACKGROUND OF THE INVENTION

This invention relates to a method of inhibiting parasitic activity by inhibiting the biosynthesis of the glycosyl phosphatidylinositol (GPI) anchor of the parasite. More particularly, the invention relates to the inhibition of parasitic activity by incorporating into the GPI anchor of the parasite an oxy-substituted fatty acid analog in place of myristate.

Glycosyl phosphatidylinositols (GPIs) anchor diverse proteins to the plasma membranes of organisms ranging from the yeasts to mammals. See, e.g., the review article by Low, *Biochem. J.* 244, 1-13 (1987). The most completely characterized GPI anchor is that of the variant surface glycoprotein (VSG) of the parasitic protozoan *Trypanosoma brucei*. See, e.g., the research article by Ferguson et al., *Science* 239, 753-759 (1988), for the complete primary structure of the GPI anchor of VSG variant 117. This parasite, in common with other African trypanosomes, evades the mammalian immune system by antigenic variation in which individual genes encoding immunologically distinct VSGs form a dense surface coat. The VSG coat acts as a macromolecular diffusion barrier which protects the parasite from lytic host-serum components.

*Trypanosoma brucei* is a protozoan bloodstream parasite responsible for African sleeping sickness which has a devastating effect on human health and on livestock production. Consequently, methods of inhibiting the activity of this and related protoazoan parasites would have significant importance to medical science and for the development of therapeutic intervention to parasitic diseases.

BRIEF DESCRIPTION OF THE INVENTION

In accordance with the present invention, a method is provided for inhibiting parasitic activity by inhibiting biosynthesis of the GPI anchor of the parasite. The method comprises incorporating into the GPI anchor of the parasite an oxy-substituted fatty acid analog in place of myristate.

The *Trypanosoma brucei* VSG has a sn-1,2-dimyristyl glycerol moiety at its COOH terminus. See, e.g., Ferguson and Cross, *J. Biol. Chem.* 259, 3011-3015 (1984); Ferguson et al., Ibid. 260, 4963-4968 (1985). This moiety is embedded in the membrane bilayer and is responsible for anchoring. According to the invention it has been found that incorporation of an oxy-substituted fatty acid analog into the VSG in place of myristate has a substantial inhibitory effect on the parasitic growth and viability in culture. Since the *Trypanosoma brucei* VSG has a strict requirement for myristate, the oxy-substituted fatty acid analog is believed to act as a competitive inhibitor of myristate in the biosynthesis of the VSG.

The oxy-substituted fatty acid analogs used in the method of the invention are selected from the group consisting of $C_{13}$ and $C_{14}$ fatty acids or alkyl esters thereof in which a methylene group normally in a carbon position from 4 to 13 is replaced with oxygen. The carboxyl carbon atom is defined herein as number 1 based on conventional nomenclature. Preferred alkyl esters of the oxy-substituted fatty acid analogs have from 1 to 6 carbon atoms in the alkyl group, e.g., methyl, ethyl, propyl, butyl, pentyl and hexyl.

Illustrative examples of the oxy-substituted fatty acid analogs used in the method of the invention are:

11-(Ethoxy)undecanoic acid
$CH_3CH_2O(CH_2)_{10}COOH$
11-(Methoxy)undecanoic acid
$CH_3O(CH_2)_{10}COOH$
12-(Methoxy)dodecanoic acid
$CH_3O(CH_2)_{11}COOH$
5-(Octyloxy)pentanoic acid
$CH_3(CH_2)_7O(CH_2)_4COOH$
10-(Propoxy)decanoic acid
$CH_3(CH_2)_2O(CH_2)_9COOH$
11-(1-Butoxy)undecanoic acid
$CH_3(CH_2)_3O(CH_2)_{10}COOH$
10-(2-Propynoxy)decanoic acid
$HC{\equiv}CCH_2O(CH_2)_9COOH$ Alternate nomenclature can be used for the above oxy-substituted fatty acid analogs. For example, the first listed compound, 11-(ethoxy)undecanoic acid, can alternatively be named 12-oxymyristic acid; and the last listed compound, 10-(2-propynoxy)decanoic acid, can alternatively be named 13-yne-11-oxy-myristic acid.

In a preferred embodiment of the invention, the oxy-substituted fatty acid analog is based on saturated $C_{13}$-$C_{14}$ fatty acids. A preferred compound in this group is 10-(propoxy)decanoic acid or 11-oxymyristic acid.

The oxy-substituted fatty acid analogs used in the method of the present invention are well-known compounds which have been previously described as useful antiviral agents. In their activity as antiparasitic agents in the present invention, these oxy-substituted fatty acid analogs function in a different manner than as antiviral agents. In their antiviral activity, these compounds serve as substrates of myristoylating enzymes, e.g. N-myristoyltransferase, in the myristoylation reaction; whereas, in their antiparasitic activity, these compounds are incorporated into the GPI anchor of the parasite. However, the antiparasitic activity may also be mediated, in part, by alteration of N-myristoylated proteins, or by some change in membrane structure caused by incorporation of the oxy-substituted fatty acid analog into phospholipids.

In illustrative examples of the invention, at a concentration of 10 $\mu M$, 10-(propoxy)decanoic acid had a striking effect on *Trypanosoma brucei* growth and viability compared to 10 $\mu M$ myristate. Titration of 1 $\mu M$ concentration of the compound also inhibited parasite growth (only one doubling in 36 hours). 12-(Methoxy)-dodecanoic acid at 10 $\mu M$ inhibited growth to the same extent as 1 $\mu M$ 10-(propoxy)decanoic acid. 5-(Octyloxy)pentanoic acid inhibited growth slightly less.

The preparation of the oxy-substituted fatty acid analogs used in the method of the invention can be carried out by methods analogous to the preparation of mixed ethers by the Williamson synthesis. Thus, an appropriate $\omega$-bromo carboxylic acid can be reacted with a suitable alcoholate.

In particular, the compounds used in the method of the invention can be produced by methods analogous to the synthesis of heteroatom-substituted analogs of stearic acid as described by Pascal and Ziering, J. Lipid Res.27, 221-224 (1986). Using these methods, the oxygen-containing analogs can be prepared by the reaction of the ω-bromo acids with alcoholic base. This can be illustrated by the preparation of 12-(methoxy)-dodecanoic acid as follows:

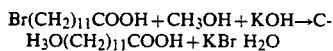

Other oxy-substituted fatty acid analog inhibitor compounds used in the method of the invention can be prepared by similar such methods by selecting appropriate alkyl and fatty acid chain lengths in the reactant compounds to produce the desired products. The foregoing type reactions are carried out in organic solvent medium at refluxing temperatures until the desired reaction is essentially complete.

The preparation and antiviral use of these oxy-substituted fatty acid analogs is described by:
Heuckeroth et al., J. Biol. Chem. 263, 2127-33 (1988);
Heuckeroth et al., Proc. Natl. Acad. Sci. USA 85, 8795-99 (1988);
Heuckeroth and Gordon, Ibid. 86, 5262-66 (1989);
Bryant et al., Ibid. 86, 865-69 (1989); and
European Patent Application 327,523, publ. Aug. 9, 1989.

Although specific methods of preparation of the oxy-substituted fatty acid analogs are described herein, it will be understood that the use of these compounds in the method of the invention is not limited to any specific method of their preparation.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments taken in conjunction with the accompanying drawings in which briefly:

FIG. 1A shows the cell free radiolabeling of GPI species with of [$^3$H]myristoyl CoA and [$^3$H]-10-(propoxy)decanoic acid CoA.

FIG. 1B shows the effects of myristate and 10-propoxy)decanoic acid on GDP-[$^3$H]Manose radiolabeled GPI intermediates.

FIG. 2A shows the incorporation of [$^3$H]myristate and [$^3$H]-10-(propoxy)decanoic acid into trypanosome lipids.

FIG. 2B shows the incorporation of [$^3$H]myristate and [$^3$H]-10-(propoxy)decanoic acid into VSG.

Figure 3A:
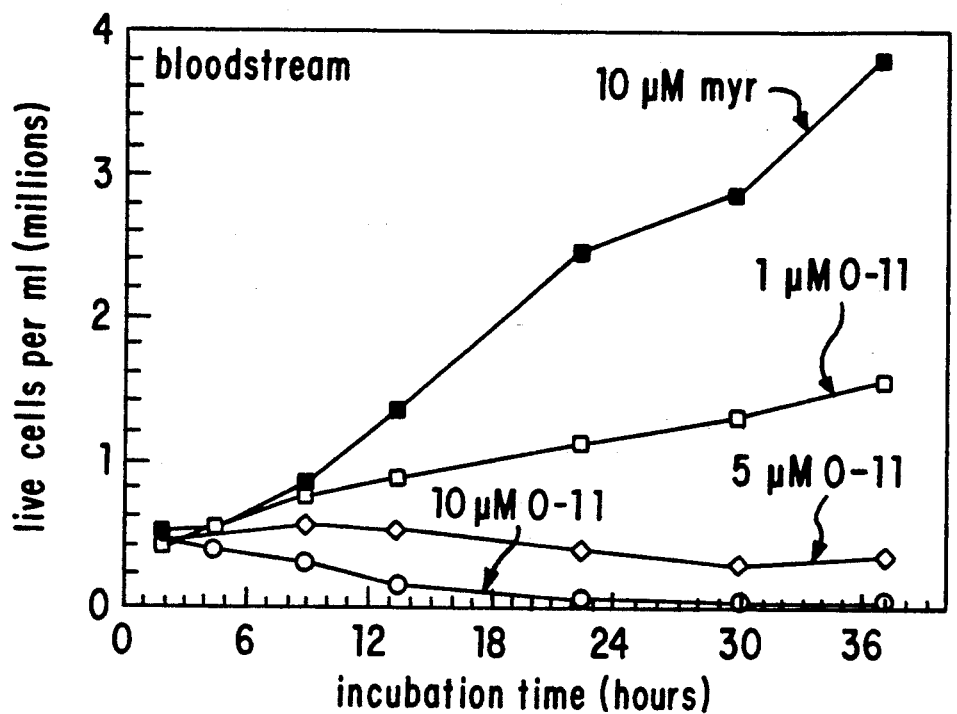
FIG. 3 is a graphical representation which shows the inhibitory results obtained by the treatment of cultures of (panel A) bloodstream and (panel B) procyclic trypanosomes with 10-(propoxy)decanoic acid.

In order to illustrate the invention in greater detail, oxy-substituted fatty acid analogs were employed in vivo and in a cell free system in the following examples to demonstrate the mechanism of myristate incorporation into the GPI anchor of Trypanosoma brucei. Although specific examples of the invention are illustrated herein, it will be understood that the invention is not limited to these specific examples.

EXAMPLES

FATTY ACID REMODELING IN THE CELL FREE SYSTEM

To determine whether oxy-substituted fatty acid analogs were substrates for fatty acid remodeling, representative oxy-substituted fatty acid analogs were added to a cell free system for glycolipid A biosynthesis [Masterson et al., Cell 56, 793-800 (1989); Masterson et al., Cell 62, 73-80 (1990)]. When cell free reactions are conducted in the presence of UDP-GlcNAc and GDP-Man, the glycan portion of glycolipid A is constructed de novo on endogenous PI bearing fatty acids longer than myristate; this produces a GPI termed glycolipid A'. Next, one fatty acid is removed from glycolipid A', yielding a lyso-GPI termed glycolipid θ. In the presence of myristoyl CoA, myristate is added to the free position of glycolipid θ, to form glycolipid A". Further fatty acid remodeling converts this species to glycolipid A, containing two myristates.

When no nucleotide sugars are present to allow de novo GPI biosynthesis, myristate is still incorporated into pre-existing glycolipid A and into a related glycolipid C, by a process thought to be acyl exchange. Glycolipid C is identical to A but has a fatty acylated inositol [Krakow et al., Mol. Biochem. Parasitol. 36, 263-270 (1989); Mayor et al., J. Biol. Chem. 265, 6164-6173 (1990); and Mayor et al., Ibid. 265, 6174-6181 (1990)]. This acyl exchange utilizes CoA derivatives of tritiated myristate analogs at least as efficiently as CoA derivatives of [$^3$H]myristate; radiolabel appears in GPI species A and C as well as in other lipids. This comparison is shown for one oxy-substituted fatty acid analog, [$^3$H]10-(propoxy)decanoic acid (for convenience, termed 0-I1; FIG. 1A, tracks 2 and 3).

If the cell free system is incubated with excess UDP-GlcNAc and GDP-Mannose before addition of [$^3$H]acyl CoA species, the de novo synthesis of GPI glycans is operative. Under these conditions myristate-containing intermediates in the biosynthetic pathway are radiolabeled, so that glycolipid A" is observed in addition to glycolipid A. Again, incorporation of [$^3$H]0-11 CoA into GPI species is as efficient as that of [$^3$H]myristoyl CoA (FIG. 1A, tracks 4 and 5). Similar results were obtained with two other oxy-substituted fatty acid analogs, 12-(methoxy)dodecanoic acid (0-13) and 5-(octoxy)pentanoic acid (0-6).

To demonstrate the de novo pathway more clearly, the cell free system was incubated with non-radiolabeled UDP-GlcNAc and [$^3$H]GDP-Man, to radiolabel early biosynthetic intermediates in the glycolipid A pathway (FIG. 1B, track I,) [Masterson et al., Cell 56, 793-800 (1989)]. Further incubation with ATP, CoA, and myristate drives the glycolipid A biosynthetic pathway through fatty acid remodeling to completion (FIG. 1B, track 4). 0-11 substituted for the myristate completes the remodeling of [$^3$H] mannose labeled GPIs with comparable efficiency, producing similar amounts of radiolabeled glycolipid A (FIG. 1B, track 5).

These data show efficient incorporation of oxy-substituted fatty acid analogs into GPIs, by fatty acid remodeling and by acyl exchange. However, fatty acid remodeling does not utilize palmitate, stearate, or an oxygen-substituted analog of palmitate (13-oxahexadecanoic acid) which has a hydrophobicity comparable to that of myristate. This indicates the specificity of the fatty acid remodeling process depends on the chain length of the substrate, rather than on its hydrophobicity.

Incorporation of [$^3$H]0-11 into qlycolioid A and VSG in cultured trypanosomes

The metabolism of oxy-substituted fatty acid analogs in living trypanosomes was also studied (FIG. 2). [$^3$H]0-11 is incorporated into numerous cellular lipids, in a pattern similar to that of [$^3$H]myristate (FIG. 2A). The spectrum of products includes compounds related to the VSG anchor, such as glycolipids A and C. GPIs were identified by comigration with standards on thin layer chromatographs, as well as by patterns of susceptibility to specific phospholipases. Thus, glycolipid A and its [$^3$H]0-11 labeled counterpart are cleaved by PI-PLC from *B. thuringiensis*; GPI-PLC from *T. brucei*; and GPI-PLD from human serum; glycolipid C and its counterpart only by GPI-PLD; using conventional conditions as described by Masterson et al., *Cell* 56, 793-800 (1989). The kinetics of labeling of the GPI species are similar with [$^3$H]0-11 and with [$^3$H]myristate; the GPIs are labeled rapidly, and by 20 min incorporation attains steady state. GPIs were also radiolabeled by [$^3$H]0-I3 and by [$^3$H]0-6. At steady state, incorporation of [$^3$H]0-11 into glycolipids A and C, or into VSG protein (FIG. 2B), occurs at less than ten percent the efficiency of [$^3$H] myristate incorporation. The other oxy-substituted fatty acid analogs tested demonstrated similar kinetics and product profile, but were incorporated to an even lesser extent (1-3% of the myristate level, in which all analogs and myristate were adjusted to the same specific activity.

The inefficient incorporation of oxy-substituted fatty acid analogs (compared to myristate) observed in vivo contrasts sharply with the cell free system, where analogs and myristate are handled similarly. Since the cell free data demonstrate that discrimination does not occur at the level of the biosynthetic pathway, factors dependent on cell integrity (e.g. fatty acid uptake or compartmentalization) must be responsible for the difference. Consistent with this observation, trypanosomes in culture do accumulate myristate at an eight-fold higher rate than they accumulate 0-11.

Results: Cell culture tests

The trypanosome has a unique and highly efficient mechanism for incorporating myristate into its VSG anchor, suggesting this fatty acid may play a crucial function in trypanosomal biology. Therefore, the effects of 0-11 and other oxy-substituted fatty acid analogs on the viability of this parasite in culture were studied for antiparasitic activity. At a concentration of 10 μM, 0-11 had a striking effect on parasite growth and viability (FIG. 3A) compared to 10 μM myristate. Mass analysis showed that after six hours of culture with 10 μM 0-11, 4% of the fatty acids on trypanosome VSG were 0-11, affecting up to 8% of the VSG molecules. Titration of the 0-11 showed that even 1 μM analog inhibited trypanosome growth (FIG. 3A); lower concentrations had a negligible effect. Oxy-substituted fatty acid analog 0-13 at 10 μM inhibited growth to the same extent as 1 μM 0- 11; analog 0-6 inhibited growth slightly less. No difference in coat morphology was observed between cells treated with 0-11 and those treated with myristate, but gross distortion of the cells is apparent (FIG. 4, compare panels C and E with panels D and F). Treated cells develop extremely large vacuolar structures, which exhibit on their *inner* membrane leaflets the arrangement of VSG and microtubules typically found on the outer surface of trypanosomes.

The toxicity of 0-11 for bloodstream trypanosomes is believed to be related to the metabolism or function of the VSG GPI, especially since similar concentrations do not effect the growth and viability of procyclic trypanosomes. However, the results cannot rule out the possibility that toxicity is mediated in part by alteration of N-myristoylated proteins, or by some change in membrane structure. The latter could be caused by incorporation of analog into phospholipids as well as into VSG. Whatever the precise mechanism of toxicity, these studies demonstrate a new and useful method of anti-trypanosome chemotherapy.

The accompanying figures further demonstrate the foregoing results as follows:

FIG. 1A: Cell free radiolabeling of GPI species with [$^3$H]myristoyl CoA and [$^3$H]0-11 CoA.

Trypanosome lysate (5×10$^8$ cell equivalents/ml) was washed, and then incubated for 5 min at 37° C. with an excess (2.5 mM; 31.7 Ci/mmol) of [$^3$H]myristoyl CoA or [$^3$H]0-11 CoA. [$^3$H]acyl CoA was prepared from [$^3$H]fatty acids using Pseudomonas se. Acyl CoA synthetase by conventional procedure as described by Masterson et al., *Cell* 62. 73-80 (1990). Samples were extracted in chloroform:methanol:water (10:10:3) [Masterson et al., *Cell* 56, 793-800 (1989)], centrifuged, and the supernatant fraction dried under nitrogen. To cleave unincorporated [$^3$H]acyl CoA, samples were boiled for 8 min. with 50 μl 11 mM DTT. Samples were extracted twice with water saturated butanol, the pooled organic extracts washed with distilled H$_2$O and 1.5×10$^7$ cell equivalents per reaction analyzed on silica gel 60 thin layer chromatography plates developed in 10:10:3 solvent. Track I, marker track, lipids labeled in vivo [$^3$H]myristate [Krakow et al., *J. Biol. Chem.* 261, 12147-12153 (1986)]; track 2, incubation with [*CoA; trac*3, incubation with [$^3$H]0-11 CoA; track 4, incubation with [$^3$H]myristoyl CoA after preincubation (8 min, 37° C.) with 1 mM each UDP-GlcNAc and GDP-Man to allow de novo GPI glycan synthesis; track 5, as track 4 but [$^3$H]0-11 CoA. In this and the following figures: 0, origin; F, solvent front; A, C, and A" are GPI species.

The bracket indicates a smear of residual [$^3$H]acyl CoA.

FIG. 1B: The effects of myristate and 0-Il on GDP-[$^3$H]Man radiolabeled GPI intermediates Lysate (5×10$^8$ cell equivalents/ml) was first incubated with I mM UDP-GlcNAc and 3 μCi/ml GDP-[$^3$H]Man (17 Ci/mmole; 0.18 μM final concentration) for 5 min at 37° C., then chased with 1 mM nonradioactive GDP-Man for 3 min at 37° C. to allow radiolabel to accumulate in glycolipids A' and θ, (track 1). To examine fatty acid remodeling, the reaction mixture was then incubated for 5 min with either no further additions (track 2), or with 0.6 mM ATP, 0.2 mM CoA and the following: track 3, no fatty acid; track 4, 1 mM myristate; track 5, 1 mM 0-11. Sample extraction and chromatography was as in FIG. 1A. GPI intermediates indicated are: A', a heterogeneous species containing two fatty acids, each longer than myristate; θ, a lyso species of A'; A", with one myristate and one longer fatty acid; and A, with two myristates. The prominent band near the front in track 5 is unidentified and appears inconsistently.

FIG. 2A: Incorporation of [$^3$H]0-11 into intact trypanosomes.

Cloned ILTat 1.3 trypanosomes, isolated from mouse blood [Bangs et al., *Proc. Natl. Acad. Sci. USA* 82, 3207–3211 (1985)], were washed once in MEM "alpha" (catalog number 320-2561 AJ, Gibco Laboratories, Grand Island, NY) supplemented with 4.4 g/l glucose, 3.9 mg/l thymidine, 13.6 mg/l hypoxanthine, 68 mg/l phenylalanine, 64 mg/l tyrosine, 10 g/l essentially fatty acid free bovine serum albumin (BSA) (Sigma Chemical Company, St. Louis, MO), 110 mg/l pyruvate, 50,000 units/l penicillin, 50 mg/l streptomycin, and 5% fetal calf serum. Cells were suspended in the same medium ($5 \times 10^7$ cells/ml) with 100 $\mu$Ci/ml [$^3$H]myristic acid (NEN; 32 Ci/mmol) or [$^3$H]0-11 (32 Ci/mmol; [Johnson et al., *Proc. Natl. Acad. Sci. USA* 87, 8511–8515 (1990)], incubated at 37.C for 80 min, and washed. Glycolipids were extracted from $10^7$ cells [Doering et al., *J. Biol. Chem.* 264, 11168–11173 (1989)] and analyzed by TLC as in FIG. 1, above. Abundant species above glycolipid C are cellular phospholipids; free fatty acids and diacyl glycerols migrate near the solvent front. Myr, myristate; A, glycolipid A; and C, glycolipid C. FIG. 2B: Incorporation of [$^3$H]myristate and [$^3$H]0-Il into VSG.

Cells labeled as in Panel A ($10^8$ a cells/ml, 90 min) were washed twice and boiled with SDS-PAGE sample buffer. Protein from cells labeled with [$^3$H]myristate ($10^6$ cell equivalents) or [$^3$H]0-11 ($10^7$ cell equivalents) was analyzed by electrophoresis on an 11% polyacrylamide gel and fluorographed. Scale (kDa) indicates migration of marker proteins, and the 59 kDa VSG band is indicated. Fatty acid radiolabel is released from VSG when gels are treated with alkali (0.2 M KOH in MeOH, 1 h, room temperature) consistent with ester-linkage to the GPI anchor. Longer exposures of a similar gel show minor species (in both lanes) that are not susceptible to alkaline hydrolysis; these could be N-myristoylated proteins.

Figure 3B:
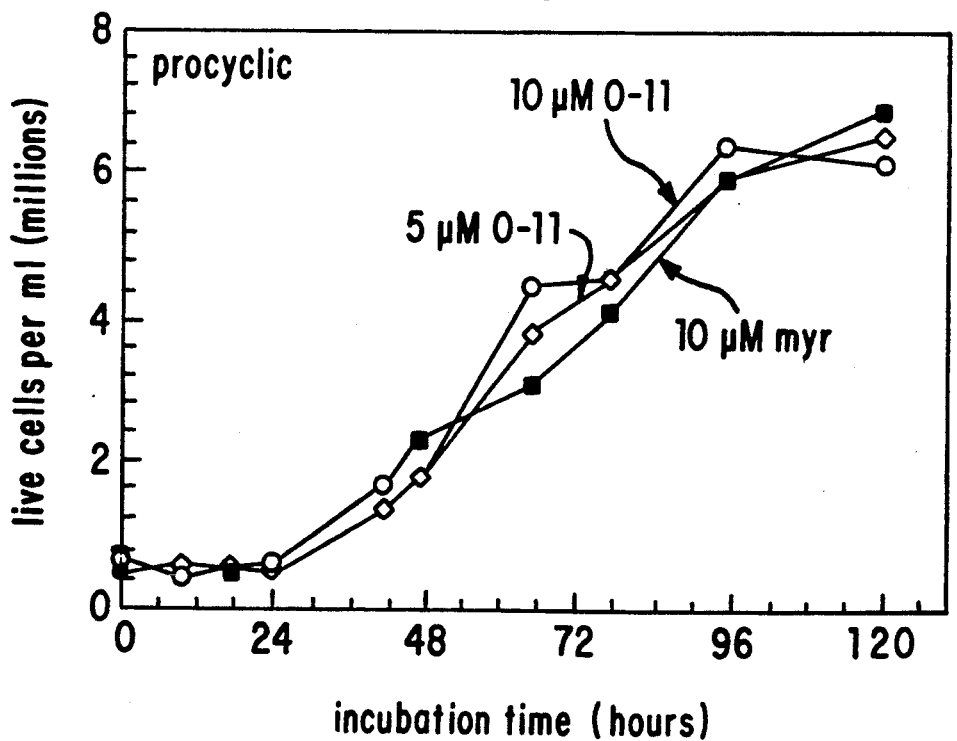
Figure 4A:
FIG. 4 shows electron micrographs of trypanosomes in culture treated either with 10 μM myristate or 5 μM 10-(propoxy)decanoic acid at various magnification in panels A to F.
Figure 4B:
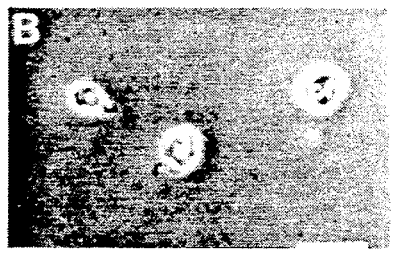
Figure 4C:
Figure 4D:
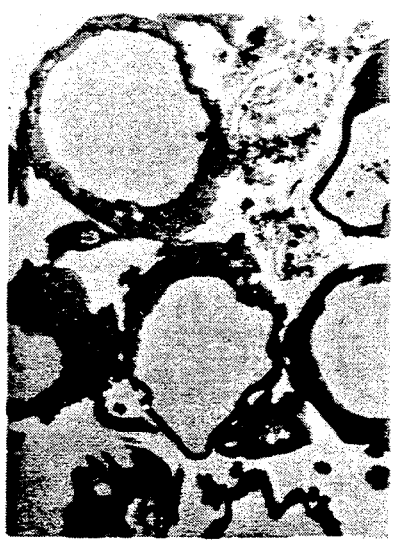
Figure 4E:
Figure 4F:
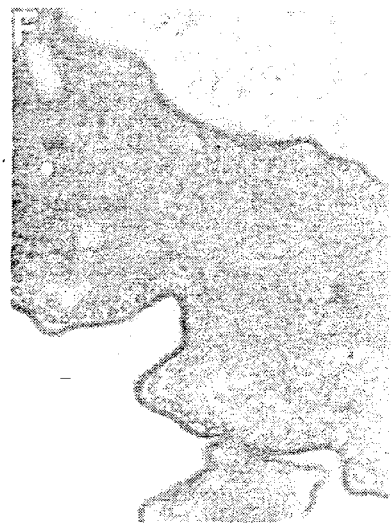

FIG. 3: Treatment of cultures of bloodstream and procyclic trypanosomes with 0-11.

Bloodstream forms: *T. brucei* strain 427 (variant 221) parasites were obtained from G.A.M. Cross (Rockefeller University). Trypanosomes were isolated from mouse blood at a parasitemia of $5 \times 10^8$ cells/ml [Masterson et al., *Cell* 56, 793–800 (1989)], and cultured (37°, 5% CO$_2$) in prewarmed medium (as in FIG. 2) containing 40 $\mu$M monothioglycerol and myristate or 0-11 as indicated. Similar growth curves were seen in five independent tests and cell counts were generally within 10%.

Procyclic trypanosomes: Strain TREU 667 (from S. Hajduk, U. of Alabama), was cultured at 28. in SM medium Cunningham, *J. Protozool.* 24(2), 325–329 (1977)]. Cultures were counted in duplicate at the times shown.

Any cell demonstrating minimal movement was scored as "live". Myristate or 0-11 [Johnson et al., *Proc. Natl. Acad. Sci. USA* 87, 8511–8515 (1990)] was added from a 1000×stock in absolute ethanol; growth curves of control cultures (0.1% ethanol) were indistinguishable from those of the cultures containing 10 $\mu$M myristate.

FIG. 4:

Bloodstream form cells were cultured for 24 hours in the presence of 10 $\mu$M myristate or 5 $\mu$M 0-11.

Panels A-B: Light micrographs were taken using phase optics on a Zeiss Axiophot instrument. Magnification is indicated by the bar in the lower right hand corner of the panel. For panels A and B, the bar is equivalent to 15 $\mu$m.

Panels C-F: Cells were prepared for electron microscopy according to the conventional procedure described by Cross *Parasitology* 7I, 393–417(1975). For panels C and D, the bar is equivalent to 2.2 $\mu$m; for panels E and F, the bar is equivalent to 0.2 $\mu$m.

The antiparasitic agents described herein can be used for administration to mammalian hosts infected with trypanosomes and the like by conventional means, preferably in formulations with pharmaceutically acceptable diluents and carriers. The amount of the active agent to be administered must be an effective amount, that is, an amount which is medically beneficial but does not present toxic effects which overweigh the advantages which accompany its use. It would be expected that the adult human dosage would normally range upward from about one milligram of the active compound. A suitable route of administration is orally in the form of capsules, tablets, syrups, elixirs and the like, although parenteral administration also can be used. Appropriate formulations of the active compound in pharmaceutically acceptable diluents and carriers in therapeutic dosage form can be prepared by reference to general texts in the field such as, for example, *Remington's Pharmaceutical Sciences,* Ed. Arthur Osol, 16th ed., 1980, Mack Publishing Co., Easton, PA.

Various other examples will be apparent to the person skilled in the art after reading the present disclosure without departing from the spirit and scope of the invention. All such other examples are intended to be included within the scope of the appended claims.

ACKNOWLEDGEMENT OF SUPPORT

The invention herein was made in part with government support under grant number AI30188-011 awarded by the National Institute of Allergy and Infectious Diseases and by a grant from Monsanto Company.

What is claimed is:

1. A method of inhibiting growth and viability of bloodstream trypanasome parasites having a GPI membrane anchor which comprises contacting said bloodstream trypanosome parasites with an oxy-substituted fatty acid analog selected from the group consisting of $C_{13}$ and $C_{14}$ fatty acids or alkyl esters thereof in which a methylene group normally in carbon position from 4 to 13 of said fatty acid is replaced with oxygen, whereby the myristate in said GPI membrane is replaced with said oxy-substituted fatty acid analog.

2. The method of claim 1 in which the trypanosome is Trypanosoma brucei.

3. The method of claim 1 in which the oxy-substituted fatty acid analog is 10-(propoxy)decanoic acids.

4. The method of claim 2 in which the oxy-substituted fatty acid analog is 10-(propoxy)decanoic acid.

5. The method of claim 2 in which the oxy-substituted fatty acid analog is 12-(methoxy)dodecanoic acid.

6. The method of claim 2 in which the oxy-substituted fatty acid analog is 5-(octyloxy)pentanoic acid.

* * * * *

UNITED STATES PATENT AND TRADEMARK OFFICE
CERTIFICATE OF CORRECTION

PATENT NO. : 5,151,445

DATED : Sept. 29, 1992

INVENTOR(S) : Joseph K. Welply, Steven P. Adams and Jeffrey I. Gordon

It is certified that error appears in the above-identified patent and that said Letters Patent is hereby corrected as shown below:

In col. 2, line 4, "onventional" should read --conventional--. In col. 6, line 26 "se" should read --sp--. In col. 6, line 40 "[CoA;trac3" should read --[$^3$H]myristoyl CoA; track 3--. In col. 6, line 52, "I" should read --1--. In col. 8, line 41 "AI30188-011" should read --AI30188-01--. In col. 8, line 58, "acids" should read --acid--.

Signed and Sealed this

Twenty-first Day of September, 1993

Attest:

BRUCE LEHMAN

Attesting Officer

Commissioner of Patents and Trademarks